US00PP36933P2

(12) United States Plant Patent
Fell

(10) Patent No.: US PP36,933 P2
(45) Date of Patent: Sep. 2, 2025

(54) ***ALOCASIA* PLANT NAMED 'Silver Wings'**

(50) Latin Name: ***Alocasia* hybrid**
Varietal Denomination: Silver Wings

(71) Applicant: David Fell, Waimanalo, HI (US)

(72) Inventor: David Fell, Waimanalo, HI (US)

( * ) Notice: Subject to any disclaimer, the term of this patent is extended or adjusted under 35 U.S.C. 154(b) by 0 days.

(21) Appl. No.: 19/183,795

(22) Filed: Apr. 19, 2025

(51) Int. Cl.
*A01H 6/10* (2018.01)
*A01H 5/02* (2018.01)

(52) U.S. Cl.
USPC ..... Plt./373

(58) Field of Classification Search
USPC ..... Plt./373
CPC ..... A01H 6/10; A01H 5/02
See application file for complete search history.

*Primary Examiner* — Keith O. Robinson
(74) *Attorney, Agent, or Firm* — James R. Holm; Plant Novelty Rights, LLC

(57) ABSTRACT

A new and distinct variety of *Alocasia* plant named 'Silver Wings' particularly distinguished by dark purplish grey leaf coloration on the adaxial surface and purplish pink leaf coloration on the abaxial surface, narrowly sagittate leaf shape, and hybrid vigor.

4 Drawing Sheets

Figure 1:
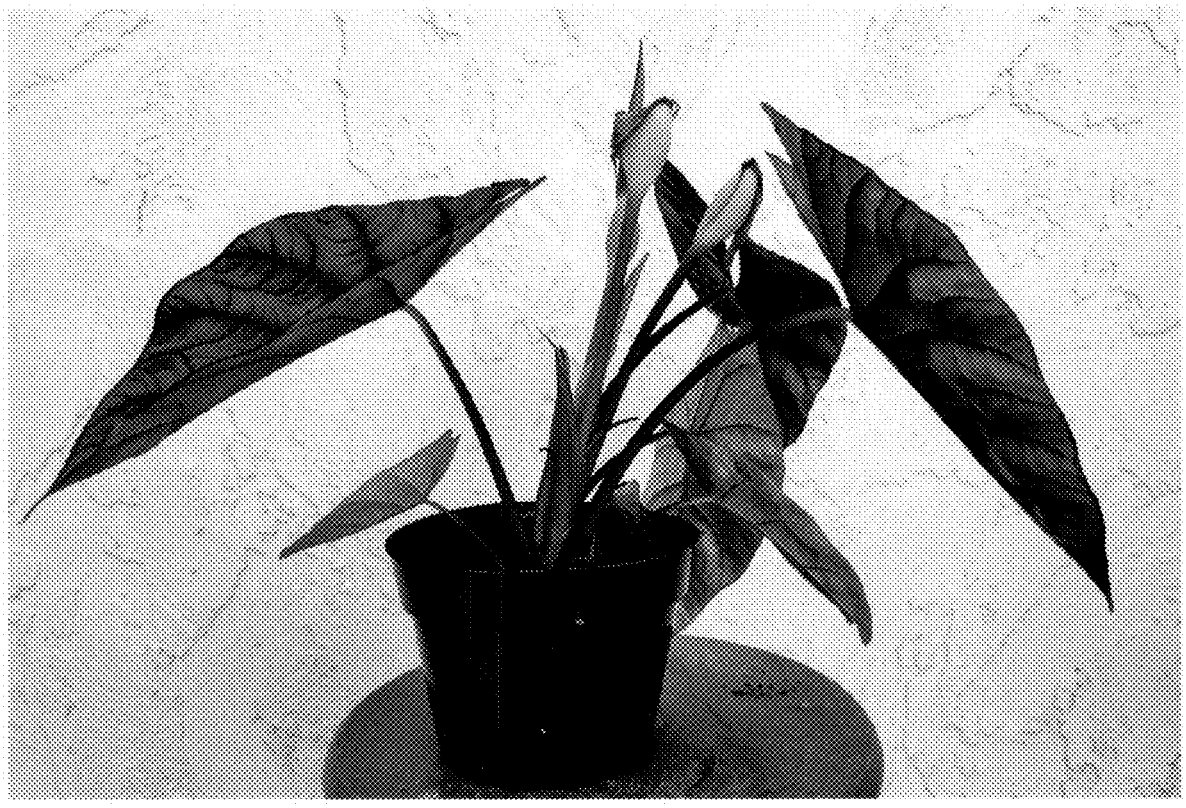

Genus and species: *Alocasia* hybrid.
Variety denomination: 'Silver Wings'.

BACKGROUND OF THE NEW PLANT

The present invention comprises a new and distinct interspecific hybrid plant of *Alocasia*, hereinafter referred to by its cultivar name 'Silver Wings'.

The new cultivar was derived from a breeding program conducted by the inventor at a nursery in Waimanalo, Hawaii. The overall purpose of the breeding program is to make new selections of *Alocasia* plants with unique foliage that are durable with a good growth rate. 'Silver Wings' is the product of a controlled cross made by the inventor in August 2022 between the *Alocasia baginda* plant named 'Silver Dragon' (unpatented) as the female parent and an unnamed and unpatented *Alocasia scalprum* plant as the male parent. 'Silver Wings' was selected in Waimanalo, Hawaii by the inventor in June 2024 as a single unique plant from amongst progeny plants derived from said cross.

The new cultivar was selected based on its distinctive leaf color pattern, leaf shape and hybrid vigor. 'Silver Wings' was first reproduced asexually by vegetative rhizome divisions in August 2023 in Waimanalo, Hawaii. Asexual propagation by vegetative rhizome divisions of the new cultivar has shown that the unique features of the new cultivar are stable and reproduce true-to-type through three successive generations.

STATEMENT REGARDING PRIOR DISCLOSURES BY THE INVENTOR

The Inventor asserts that no publications or advertisements relating to sales, offers for sale, or public distribution occurred more than one year prior to the effective filing date of this application. Any information about the claimed plant would have been obtained from a direct or indirect disclosure from the Inventor. The Inventor claims a prior art exemption under 35 U.S.C. 102(b)(1) for disclosures and/or sales that fall within a one-year grace period prior to the filing date.

SUMMARY OF THE INVENTION

The new *Alocasia* cultivar has not been observed under all possible environmental conditions. The phenotype may vary somewhat with variations in environment such as temperature, day length, light intensity, water status, fertilizer rate and type, without, however, any variance in genotype.

The following are the most outstanding and distinguishing characteristics of this new *Alocasia* cultivar. The combination of these characteristics distinguishes 'Silver Wings' as a new and distinct variety of *Alocasia*:

1. Dark purplish grey leaf coloration on the adaxial surface and purplish pink leaf coloration on the abaxial surface;
2. Narrowly sagittate leaf shape; and
3. Hybrid vigor.

'Silver Wings' can be compared to its female parent by having a similar leaf coloration on the adaxial surface and by having a similar leaf shape and similar leaf coloration of its male parent on the abaxial leaf surface. 'Silver Wings' is distinctly different from all current commercial *Alocasia* varieties due to its unique leaf color pattern which is a combination of the leaf color characteristics observed on both parents.

DESCRIPTION OF THE PHOTOGRAPHS

This new *Alocasia* cultivar is illustrated by the accompanying-colored photographs which show the overall appearance and distinct characteristics of the plant. The colors shown are as true as can be reasonably obtained by conventional photographic procedures. The photographs are of a 4-month-old plant grown in a 6-inch container in a shade house in Waimanalo, Hawaii under 73 percent shade (approximately 4800 foot candles) with a temperature range of 60 to 90 degrees Fahrenheit and a humidity range of 40 to 80 percent. Colors in the photographs may differ slightly from the color values cited in the botanical description which accurately describes the colors of the new variety.

FIG. 1. shows a side view of the overall plant form and foliage of 'Silver Wings'.

Figure 2:
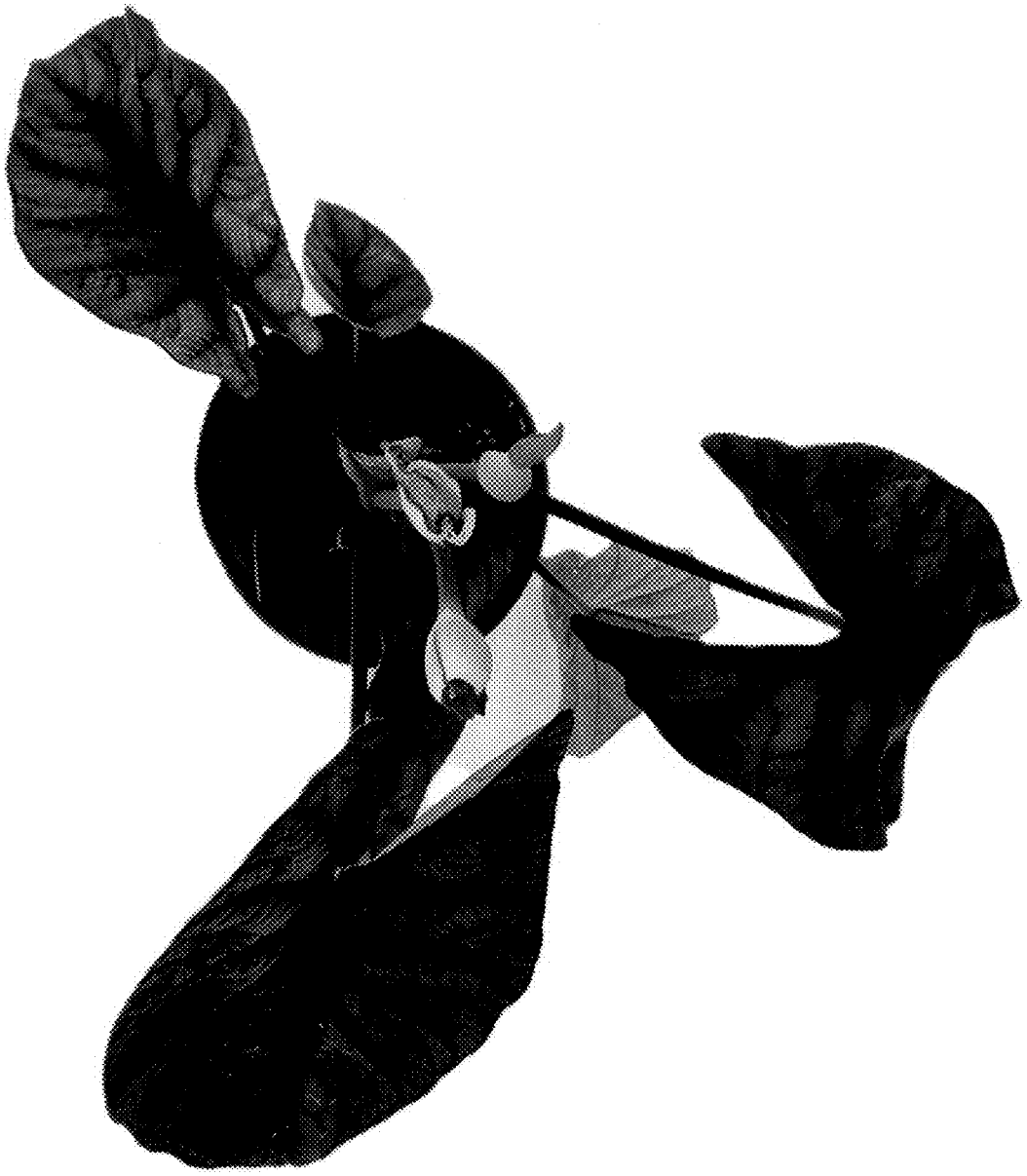

FIG. 2. shows a top view of the overall plant form and foliage of 'Silver Wings'.

Figure 3:
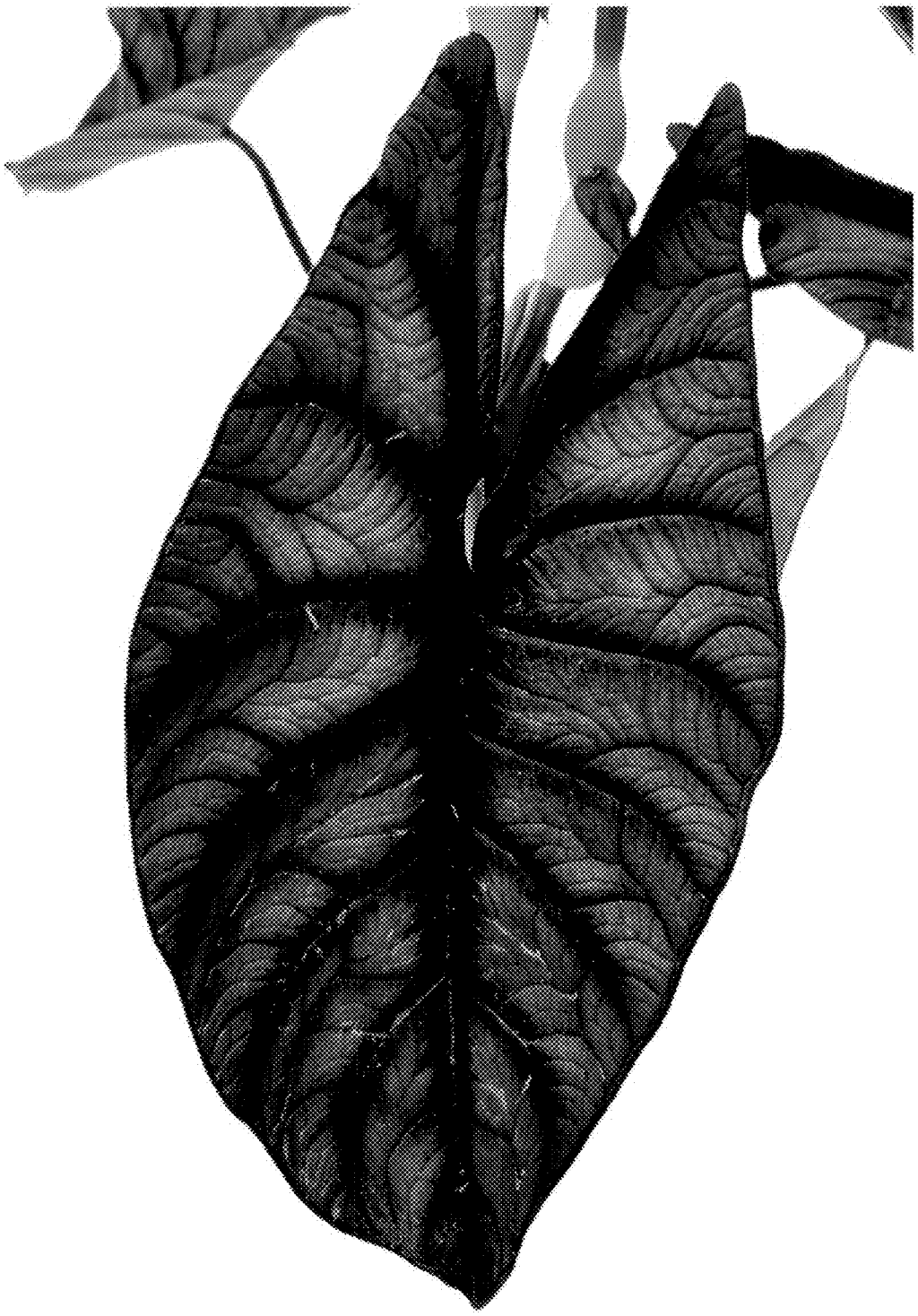

FIG. 3. shows a closeup of the adaxial surface of a mature leaf of 'Silver Wings'.

Figure 4:
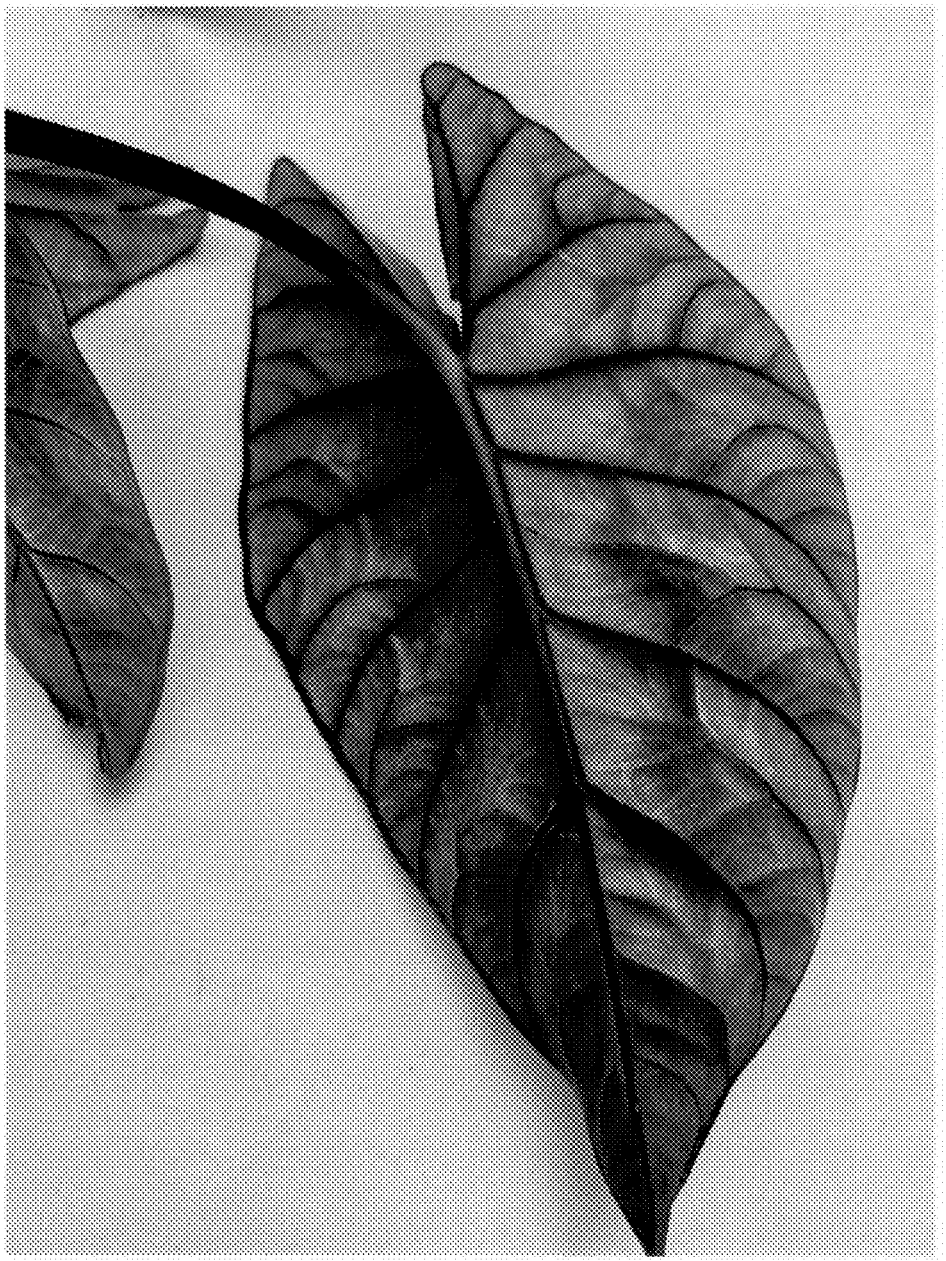

FIG. 4. shows a closeup of the abaxial surface of a mature leaf of 'Silver Wings'.

DESCRIPTION OF THE NEW VARIETY

In the following description, color references are made to The Royal Horticultural Society Colour Chart, Sixth Edition, except where general color terms of ordinary dictionary significance are used.

The following observations and measurements describe plants grown under 73 percent shade (approximately 4800-foot candles) in a shade covered greenhouse in Waimanalo, Hawaii. Detailed descriptions were taken in March 2025 from a 4-month-old plant grown in a 6-inch container. Measurements and numerical values represent averages of typical plant types.

DETAILED BOTANICAL DESCRIPTION

Classification:

*Family*.—Araceae.

*Botanical*.—*Alocasia* hybrid.

*Common*.—Alocasia or Elephant Ear.

*Denomination*.—'Silver Wings'.

General description:

*Plant type*.—Rhizomatous tropical perennial.

*Plant form*.—Upright with one primary (dominant) rhizomatous branch, no secondary branching observed.

*Height from soil level to top of foliar plane*.—Approximately 25.0 cm.

*Plant spread*.—Approximately 48.0 cm.

*Primary branch diameter*.—3.0 cm at the base above the soil level.

*Growth rate*.—Medium to fast.

*Propagation type*.—Vegetative rhizome divisions and meristem tissue culture.

*Roots*.—Thick, fleshy and fibrous, colored 155D (yellowish white).

Foliage description:

*Quantity of leaves*.—8.

*Arrangement*.—Alternate to spiraled.

*Attachment*.—Petiolate.

*Division*.—Simple.

*Cataphylls* (*observed on young inflorescence*).—General description: Cataphylls are not persistent and wither and become brown and desiccated within a few days of inflorescence emergence. Length: 12.5 cm. Width: 3.5 cm at the base then narrowing to 1.5 cm at 1.0 cm below the apex of the cataphyll. Shape: Lanceolate. Texture and luster: Inner surface: Smooth, glabrous and shiny. Outer surface: Corrugated, glabrous and matte. Color: Inner surface: Mostly white and translucent with reticulated venation colored 183A (dark red). Outer surface: Mostly white and translucent with a midrib colored 187A (dark red) at the apex and reticulated venation colored 183A (dark red).

*Lamina* (*mature foliage*).—Shape: Narrowly sagittate. Length: Approximately 26.0 cm to 28.0 cm when measured along the center axis of the foliar plane. Width: Approximately 12.5 cm to 14.5 cm at the widest point above the lobes. Orientation: Initially held vertically and becoming pendulous when mature. Appearance: Incised venation on the adaxial surface with bullate leaf tissue between the venation. Apex shape: Narrowly acuminate. Base: Saggitate. Lobes: Length: About 10.0 cm when measured from the apex of the sinus to the base of the lobe. Width: About 6.5 cm when measured at the apex of the sinus across to the edge of the lamina. Margins: Entire. Texture and luster: Abaxial surface: Slightly rugose, glabrous and matte. Adaxial surface: Rugose, glabrous and satiny. Venation pattern: Pinnate, one primary vein (midvein) and approximately 14 secondary veins with numerous veinlets appearing in a netted pattern. Color: Adaxial surface: Interveinal areas: N186A (dark purplish grey) flanking the secondary veins and primary vein; N189A to N189B (dark greyish green) centered between the secondary veins. Primary vein: N186A (dark purplish grey). Secondary veins: N186A (dark purplish grey). Veinlets: N186A (dark purplish grey). Abaxial surface: Interveinal areas: 186C (dark purplish pink). Primary vein: 193A (pale yellow green) diffused with 187A (dark red) from the petiole attachment through the center before transitioning to solid 187A towards and at the apex. Secondary veins: 187A (dark red). Veinlets: 187A (dark red).

*Petioles* (*mature foliage*).—Strength: Flexible. Aspect: Initially held upright and then arching downwards with development. Length: Approximately 22.5 cm. Diameter: Distally: 0.4 cm at point of attachment to the lamina. Proximally (above wing apex): Approximately 0.8 cm. Texture and luster: Smooth, glabrous and shiny. Color: N79A to N79B (dark purplish red) from the base to near the point of attachment to the lamina; 193A (pale yellow green) diffused with N79B just below the attachment to the lamina. Wings: Length: Approximately 4.5 cm. Width: Approximately 2.5 cm at the base. Color (both inner and outer surfaces): 193A (pale yellow green) diffused with N79B (dark purplish red).

Inflorescence:

*Type*.—Spadix surrounded by a spathe, male portion held above female portion.

*Peduncle*.—Length: 16.0 cm. Diameter: 0.8 cm, widening towards the base of the spadix, 1.5 cm. Color: Translucent, 183C (moderate red) with faint undertones of 155A (pale yellow green) and 144C just below the spadix.

*Spathe*.—Shape: Wedge-shaped above female zone, elliptic in shape surrounding female zone. Margin: Entire. Length: 10.5 cm above female zone, 3.0 cm surrounding female zone. Width: 2.2 cm above female zone and gradually tapering towards the apex, 2.0 cm surrounding female zone. Color: Above female zone: 145B (light yellow green) with tints 187C (dark red) within the venation and along the margins. Surrounding female zone: 1C (light greenish yellow) with tints of 187C (dark red) along the margin.

*Spadix*.—Length: 9.3 cm. Appendix zone: Shape: Lanceolate. Apex: Obtuse. Length: 5.3 cm. Width: 1.6 cm. Color: 159B (pale orange yellow). Male zone: Shape: Cylindrical. Length: 2.7 cm. Width: 1.3 cm. Color: 158B (pale yellow). Female zone: Shape: Conical. Length: 1.3 cm. Width: 1.0 cm. Color: 142A (strong yellow green).

Cold tolerance: None observed.
Disease and pest tolerance: None observed.
Fruit and seed set: None observed.
Drought tolerance: None observed.

What is claimed is:

1. A new and distinct variety of *Alocasia* plant named 'Silver Wings', substantially as illustrated and described herein.

* * * * *